United States Patent [19]

Kawashima et al.

[11] Patent Number: 4,726,966

[45] Date of Patent: Feb. 23, 1988

[54] PREPARATION OF COATED GRANULAR IBUPROFEN MICROSPHERE

[75] Inventors: Yoshiaki Kawashima; Hirofumi Takeuchi; Toshiyuki Niwa; Tetsurou Handa, all of Gifu, Japan

[73] Assignee: Showa Shinyaku Co., Ltd., Nagoya, Japan

[21] Appl. No.: 934,566

[22] Filed: Nov. 25, 1986

[30] Foreign Application Priority Data

Nov. 27, 1985 [JP] Japan ................................ 60-267021

[51] Int. Cl.$^4$ ............................................. B01J 13/02
[52] U.S. Cl. ............................... 427/213.36; 424/462; 424/497; 514/570; 514/963; 514/974
[58] Field of Search ................... 264/4.6; 427/213.36; 424/462, 497; 514/963, 974

[56] References Cited

U.S. PATENT DOCUMENTS 3,737,337  6/1973  Schnoring et al. ............. 264/4.6 X
3,859,228  1/1975  Morishita et al. ............. 427/213.36
4,457,907  7/1984  Porter ........................ 424/497 X

FOREIGN PATENT DOCUMENTS 2453640  12/1980  France ............................ 424/497

Primary Examiner—Richard D. Lovering
Attorney, Agent, or Firm—Oblon, Fisher, Spivak, McClelland & Maier

[57] ABSTRACT

This invention provides a simple method for preparing granular ibuprofen microsphere whose surface is coated with acrylic acid resin. By this method granulation of ibuprofen and coating of its surface can be simultaneously accomplished. Namely, the method of preparation includes the steps of: (a) dissolving ibuprofen with acrylic acid resin into lower aliphatic alcohol, acetone, methylene chloride or N,N-dimethylformamide; and (b) depositing coated granular ibuprofen microsphere by mixing the solution of step (a) with water and by stirring the mixed solution.

19 Claims, No Drawings

PREPARATION OF COATED GRANULAR IBUPROFEN MICROSPHERE

BACKGROUND OF THE INVENTION

The present invention relates to a preparation of granular ibuprofen microsphere whose surface is coated.

Ibuprofen is a compound which is widely used as nonsteroidal antifebriles, anodynes and anti-inflammatory drugs, and which has the following formula:

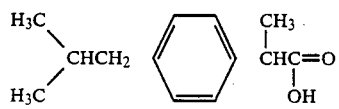

Ibuprofen is insoluble in water and is white crystalline powder (melting point 75° to 77° C.) in the ordinary state. Although ibuprofen is usually used as a powdery oral drug, it has the peculiar taste and irritating smell, thus strongly stimulating the tip of a tongue. For this reason, it has been difficult to prescribe it especially to an infant.

In order to alleviate a stimulus to the tip of a tongue, ibuprofen is usually granulated and coated. In general methods of the preparation, however, granulation and coating of ibuprofen are not simultaneously accomplished, i.e., first granulating ibuprofen and then coating the surface thereof. Thus, the process of the preparation has been complicated. Furthermore, since ibuprofen is insoluble in water, it is difficult to treat it.

DESCRIPTION OF THE INVENTION

The object of the invention is to provide a simple methods of preparation of granular ibuprofen microsphere whose surface is coated, and more particularly to provide a method of preparation in which granulation of ibuprogen and coating of its surface can be simultaneously accomplished.

The above and other related objects are realized by a preparation method including the steps of: (a) dissolving ibuprofen with acrylic acid resin into lower aliphatic alcohol, acetone, methylene chloride or N,N-dimethylformamide; and (b) depositing coated granular ibuprofen microsphere by mixing the solution of step (a) with water and by stirring the mixed solution.

The invention is now explained in detail. In this invention, powdery ibuprofen is dissolved with acrylic acid fresin into lower aliphatic alcohol, acetone, methylene chloride or N,N-dimethylformamide. Here, the lower aliphatic alcohol can be any one which contains 1 to 4 carbon atoms such as ethanol, methanol, propanol, 2-propanol and butanol; but ethanol is preferable. Acrylic acid resin can be any enteric film coating agent or retard film coating agent which is soluble in water. It may be, for example, a copolymer of acrylate or methacrylate as shown in a structural formula I or II;

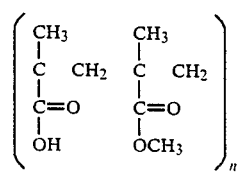

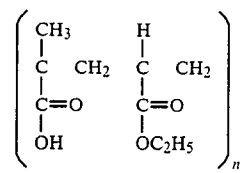

in which molar ratio of acid:ester is preferably 1:1 to 1:2. This copolymer can be partially denaturated or copolymerized with small amounts of another monomer: for example, a quaternary ammonium group-containing copolymer as shown in formula (III);

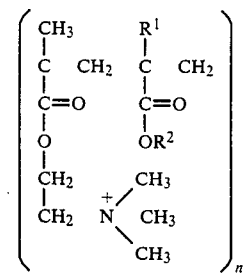

in which:
$R^1$ denotes —H or —$CH_3$; and
$R^2$ denotes —$CH_3$ or —$C_2H_5$.

In this case, the molar ratio of ammonium group:ester is 1:20 to 1:40. The molecular weight of the copolymer is usually 135,000 to 200,000. The amount of this resin can be from 2 to 100 weight % (wt%) with respect to ibuprofen, but is preferably 7 to 50 wt%. If the amount of the resin is too small, ibuprofen is not sufficiently coated, and if too large, it is not efficiently granulated. Dissolution of ibuprofen and acrylic acid resin into lower aliphatic alcohol is accomplished by stirring for 5 to 60 minutes at room temperature. Ibuprofen and acrylic acid resin can be either simultaneously or successively added to alcohol. The final concentration of ibuprofen in the solution should be adjusted within the range of between 10 and 50 wt%, but is preferable at 30 to 40 wt%.

The alcohol solution prepared as mentioned above is mixed with water and then stirred so as to deposit granular ibuprofen microsphere coated with acrylic acid resin. The amount of water is over 300 wt% with respect to the alcohol solution, but is preferable at over 1,000 wt%. If the amount is too small, granular ibuprofen with high quality cannot be obtained.

The alcohol solution and water may be previously mixed and then stirred, or the alcohol solution may be added to water with stirring. The temperature is between 5° to 40° C. while stirring and the stirring time is 5 to 60 minutes. The solution may be stirred, for example, by a shaker, a magnetic stirrer or a stirring blade, but is preferably stirred by a stirring blade.

If a surfactant exists in the reaction system while stirring, ibuprofen is efficiently granulated and coated with acrylic acid resin so that granular ibuprofen with high quality can be obtained. The surfactant can be chosen from among anionic ones such as sodium laurylsulfate, sodium benzenesulfonate, sodium laurylbenzenesulfonate and sodium oleate, cationic ones such as cetyltrimethylammonium bromide or nonionic ones such as polyethyleneglycol (molecular weight 300 to 8,000), polyoxyethylene sorbitan fatty acid ester, monoester or triester of oleic acid, sorbitan fatty acid ester and sucrose-fatty acid ester; but nonionic surfactants with 6 to 15 of HLB (hydrophil-lipophil balance) are preferable since granular ibuprofen with uniform size can be obtained. The amount of surfactant is usually 0.2 to 8 wt% with respect to ibuprofen, and preferably 1 to 2 wt%. If the amount is too small, the surfactant does not work effectively, a nd on the contrary, if too large, it is uneconomic because the effectiveness is not enhanced.

By the above treatment, granular ibuprofen microsphere coated by acrylic acid resin is deposited from the solution. When the alcoholic solution of ibuprofen is mixed with water, it first becomes an O/W (oil/water) type emulsion; i.e., droplets of the alcohol solution are formed and ethanol moves from droplets to water phase little by little, and then the ibuprofen crystal is deposited and coated with acrylic acid resin. The grain size of salvaged ibuprofen is normally 10 to 2,000 micrometers. After stirring, granular ibuprofen microsphere is recovered from the mixture by the solid-liquid separation, and then is washed with water and dried if necessary.

EXAMPLES 1 TO 8

5.0 g of powdery ibuprofen and 0.5 g of a coating agent of acrylic acid resin shown in Table 1 are added to 10 ml of ethanol in a 50 ml glass vessel; when the addition is complete, stirring by a magnetic stirrer is continued for 1 hour at room temperature in order to completely dissolve them.

At room temperature 200 ml of water with a surfactant shown in Table 1 is stirred in a 500 ml glass vessel with a stirring blade and a baffle, and the ethanol solution of ibuprofen is added thereto. Stirring is continued for 30 minutes and then granular ibuprofen microsphere is deposited.

After stirring, the mixture is filtered with suction in order to recover granules of ibuprofen microsphere, which are then washed with water and dried in a desiccator. By these processes, granular ibuprofen microspheres coated with acrylic acid resin are obtained.

Table 1 shows the average grain diameter, yield, result of coating test, existence of stimulus to the tip of a tongue in oral administration and existence of deterioration of obtained granular ibuprofen microsphere in examples 1 to 8.

TABLE 1

| No. | Sort of Coating Agent (Note 1) | Surfactant Sort (Note 2) | Surfactant Quantity of Addition (wt/vl %) (Note 3) | Average Grain Diameter (μm) | Yield (%) | Coating Test (Rate of Dissolution) (Note 4) | Stimulus to the Tip of Tongue | Deterioration of Ibuprofen |
|---|---|---|---|---|---|---|---|---|
| EX 1 | A |   | 0 | 350 | 95 | 4.70 | NO | NO |
| EX 2 | B |   | 0 | 400 | 85 | 7.00 | NO | NO |
| EX 3 | A | 1 | 0.001 | 250 | 95 | 5.50 | NO | NO |
| EX 4 | A | 1 | 0.025 | 150 | 95 | 6.80 | NO | NO |
| EX 5 | B | 2 | 0.001 | 300 | 80 | 9.00 | NO | NO |
| EX 6 | C | 1 | 0.025 | 600 | 95 | 4.70 | NO | NO |
| EX 7 | D | 2 | 0.025 | 650 | 95 | 2.00 | NO | NO |
| EX 8 | D | 3 | 0.05 | 400 | 95 | 3.40 | NO | NO |

(Note 1) Various Coating Agents
A a copolymer of methacrylic acid and methyl methacrylate m.w. 135,000 (Rohm Pharma trademark EudragitS100)
B a copolymer of methacrylic acid and ethyl acrylate m.w. 200,000 (Rohm Pharma trademark EudragitL100-55)
C a copolymer of quaternary ammonium group-containing acrylate and methacrylate m.w. 150,000 (Rohm Pharma trademark EudragitRL100)
D a copolymer of quaternary ammonium group-containing acrylate and methacrylate m.w. 150,000 (Rohm Pharma trademark EudragitRS100)
(Note 2) Various Surfactants
1 sucrose-fatty acid ester type (DAIICHIKOGYO trademark DK-esterF-110)
2 sucrose-fatty acid ester type (DAIICHIKOGYO trademark DK-esterF-90)
3 sucrose-fatty acid ester type (DAIICHIKOGYO trademark DK-esterF-70)
(Note 3) Amount of surfactant added weight/volume % with respect to water
(Note 4) Coating test (Rate of Dissolution) unit ng/ml min Since ibuprofen does not deteriorate by granulation, its efficiency and safety as a medicine is unchanged. Furthermore, the coating agent is destroyed after a certain period of time has elapsed since the oral administration, so that ibuprofen is absorbed into blood stream at the same rate as uncoated one. Although there is a similar method of granulation which is generally known, i.e., spherical crystal-agglomeration method, a liquid bridging agent is indispensable and coating of ibuprofen can not be accomplished simultaneously with granulation in the method.

EXAMPLES

Examples of this invention are described hereinafter. Since there may be many modifications, however, without departing from the scope of the invention, the examples below are not intended to limit the invention to the examples, but are intended to illustrate the invention more clearly.

I claim:

1. A method for preparing coated granular ibuprofen microsphere, the method comprising of the following steps:
    (a) dissolving ibuprofen with acrylic acid resin in ethanol; and
    (b) depositing coated granular ibuprofen microsphere by mixing the solution of step (a) with water and by stirring the mixed solution.

2. The method as claimed in claim 1, wherein the acrylic acid resin is an enteric film coating agent or a retard film coating agent which is soluble in water.

3. The method as claimed in claim 2 wherein the acrylic acid resin is a copolymer of an acrylate or a methacrylate or a quaternary ammonium group-containing copolymer of an acrylate or a methacrylate.

4. The method as claimed in claim 3, wherein the molar ratio of an acid:ester of acrylate or a methacrylate is 1:1 to 1:2.

5. The method as claimed in claim 3, wherein the molar ratio of an ammonium group: ester of acrylate or a methacrylate is 1:20 to 1:40.

6. The method as claimed in claim 1, wherein the amount of acrylic acid resin is 2 to 100 wt % with respect to ibuprofen.

7. The method as claimed in claim 1, wherein the concentration of ibuprofen in the ethanol solution is 10 to 50 wt %.

8. The method as claimed in claim 1, wherein the amount of water added is over 300 wt % with respect to the ethanol solution in step (b).

9. The method as claimed in claim 1, wherein a surfactant is present in step (b).

10. The method as claimed in claim 9, wherein the acrylic acid resin is an enteric film coating agent or a retard film coating agent which is soluble in water.

11. The method as claimed in claim 10, wherein the acrylic acid resin is a copolymer of an acrylate or a methacrylate or a quaternary ammonium group-containing copolymer of an acrylate or a methacrylate.

12. The method as claimed in claim 11, wherein the molar ratio of an acid:ester of acrylate or a methacrylate is 1:1 to 1:2.

13. The method as claimed in claim 11, wherein the molar ratio of an ammonium group:ester of acrylate or a methacrylate is 1:20 to 1:40.

14. The method as claimed in claim 9, wherein the amount of acrylic acid resin is 2 to 100 wt % with respect to ibuprofen.

15. The method as claimed in claim 9, wherein the concentration of ibuprofen in the ethanol solution is 10 to 50 wt %.

16. The method as claimed in claim 9, wherein the amount of water added is over 300 wt % with respect to the ethanol solution in step (b).

17. The method as claimed in claim 9, wherein HLB value of the surfactant is 6 to 15.

18. The method as claimed in claim 9, wherein the amount of the surfactant added is 0.2 to 8 wt % with respect to ibuprofen.

19. The method as claimed in claim 9, wherein said surfactant is sucrose-fatty acid ester.

* * * * *